United States Patent
Igo et al.

(10) Patent No.: US 7,462,641 B2
(45) Date of Patent: Dec. 9, 2008

(54) (2S,4S)-4-FLUORO-1-[4-FLUORO-BETA-(4-FLUOROPHENYL)-L-PHENYLALANYL]-2-PYRROLIDINECARBONITRILE P-TOLUENESULFONIC ACID SALT AND ANHYDROUS CRYSTALLINE FORMS THEREOF

(75) Inventors: David H Igo, Durham, NC (US); Paul R Johnson, Durham, NC (US); Daniel E Patterson, Durham, NC (US); Amarjit Sab Randhawa, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 283 days.

(21) Appl. No.: 10/565,294

(22) PCT Filed: Jul. 19, 2004

(86) PCT No.: PCT/US2004/023263

§ 371 (c)(1),
(2), (4) Date: Jan. 20, 2006

(87) PCT Pub. No.: WO2005/009956

PCT Pub. Date: Feb. 3, 2005

(65) Prior Publication Data

US 2007/0066677 A1    Mar. 22, 2007

Related U.S. Application Data

(60) Provisional application No. 60/488,902, filed on Jul. 21, 2003.

(51) Int. Cl.
*A61K 31/40*      (2006.01)
*A61K 31/401*     (2006.01)
*C07D 207/46*     (2006.01)

(52) U.S. Cl. ..................... 514/423; 548/540

(58) Field of Classification Search ................ 548/540; 514/423

See application file for complete search history.

(56) References Cited

U.S. PATENT DOCUMENTS 7,132,443 B2 *   11/2006   Haffner et al. ............. 514/423

FOREIGN PATENT DOCUMENTS

WO        03/002531        1/2003

OTHER PUBLICATIONS

Augustyns, K. et al., "The Unique Properties of Dipeptidyl-Peptidase IV (DPP IV/CD26) and the Therapeutic Potential of DPP IV Inhibitors," *Current Medicinal Chemistry*, V6, N4, 1999, pp. 311-327.

* cited by examiner

*Primary Examiner*—Joseph McKane
*Assistant Examiner*—Jason M Nolan
(74) *Attorney, Agent, or Firm*—R. (Steve) Thomas

(57) ABSTRACT

The present invention includes anhydrous crystalline forms of (2S,4S)-4-fluoro-1-[4-fluoro-β-(4-fluorophenyl)-L-phenylalanyl]-2-pyrrolidinecarbonitrile p-toluenesulfonic acid salt.

2 Claims, 6 Drawing Sheets

Powder X-ray diffraction pattern of anhydrous form 1 tosylate salt

Powder X-ray diffraction pattern of HCl salt

Powder X-ray diffraction pattern of HCl salt after exposure to 95%RH

FT Raman spectrum of anhydrous Form 1 tosylate salt

Moisture Sorption of anhydrous form 1 tosylate salt

Moisture Sorption of HCl salt

(2S,4S)-4-FLUORO-1-[4-FLUORO-BETA-(4-FLUOROPHENYL)-L-PHENYLALANYL]-2-PYRROLIDINECARBONITRILE P-TOLUENESULFONIC ACID SALT AND ANHYDROUS CRYSTALLINE FORMS THEREOF

This application is filed pursuant to 35 U.S.C. § 371 as a United States National Phase Application of International Application No. PCT/US2004/023263 filed Jul. 19, 2004, which claims priority from US 60/488,902 filed Jul. 21, 2003.

FIELD OF THE INVENTION

The present invention relates to particular forms, for example, anhydrate and hydrated forms of fluoro cyanopyrrolidine compounds. More particularly, the present invention relates to one (1) solid state anhydrous form of (2S,4S)-4-fluoro-1-[4-fluoro-β-(4-fluorophenyl)-L-phenylalanyl]-2-pyrrolidinecarbonitrile p-toluenesulfonic acid salt. This compound is an inhibitor of serine proteases, such as dipeptidyl peptidases, and are useful in the treatment of disorders, for example metabolic disorders, such as hyperglycosemia and/or other conditions of diabetes. The particular form disclosed herein demonstrates unexpectedly beneficial physical properties for use as commercial medicaments.

BACKGROUND OF THE INVENTION

International Patent Application PCT/US02/20471 having an international filing date of 26 Jun. 2002, and published as WO 03/02531 on 9 Jan. 2003, discusses serine proteases including Dipeptydyl Peptidase IV (DPP IV) and compounds that demonstrate activity as inhibitors of DPP IV. This published application, which is herein incorporated by reference, discloses heterocyclic compounds, including (2S,4S)-4-fluoro-1-[4-fluoro-β-(4-fluorophenyl)-L-phenylalanyl]-2-pyrrolidinecarbonitrile hydrochloride.

As noted in the above-referenced publication, the (2S,4S)-4-fluoro-1-[4-fluoro-β-(4-fluorophenyl)-L-phenylalanyl]-2-pyrrolidinecarbonitrile hydrochloride demonstrates inhibition activity of DPP IV. Problems exist with several salts forms of this compound, however, due to the absorption of very large amounts of water at commercially expected exposure humidities if utilized in a medicament (e.g., 20-75% relative humidity (RH)).

Additionally these salts present other problems due to an inability to be isolated as crystalline solids. As a result, suitability of these salts as a commercial medicament would be compromised unless special handling and storage procedures were instituted.

The present inventors have now identified a novel form (2S,4S)-4-fluoro-1-[4-fluoro-β-(4-fluorophenyl)-L-phenylalanyl]-2-pyrrolidinecarbonitrile p-toluenesulfonic acid salt that is commercially suitable as a serine protease inhibitor, such as dipeptidyl peptidases inhibitor, such as DPP-IV inhibitors.

The compound of the present invention may be prepared in crystal form and therefore have enhanced physical stability. More specifically, the p-toluenesulfonic acid salt of the present invention sorbs much lower amounts of water when exposed to a broad range of humidities and can be prepared in a physically stable crystal form, thus enhancing its suitability as a medicament.

SUMMARY OF THE INVENTION

The present invention includes forms of the compound of Formula (I):

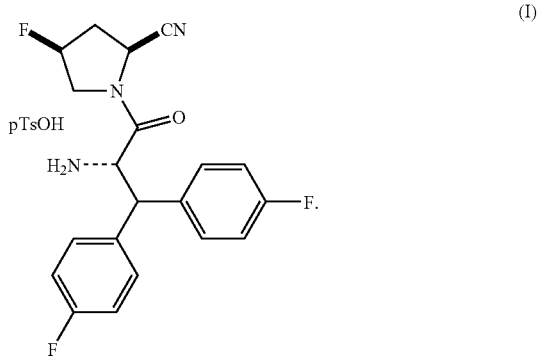

(I)

Preferably, the present invention includes one (1) solid state form, namely form 1. Most preferably, the present invention includes anhydrous form 1, which demonstrates the physical characteristics desired for commercial development as a medicament. More specifically, anyhdrous form 1 is crystalline, is thermodynamically stable, and provides a favorable moisture sorption profile.

The present invention includes anhydrous, hydrated, or solvated forms of a compound of Formula I,

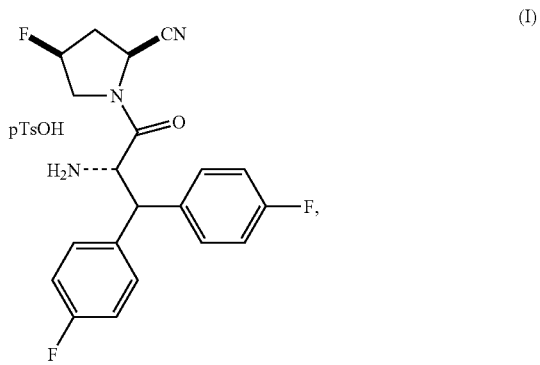

(I)

including mixtures thereof. Preferably the compound is the anhydrate form. As examples of the preferred compound of the present invention, anhydrous form 1 maybe characterized by, among other properties, a decomposition temperature of about 240-250° C. when heated at 10°/minute.

One embodiment of the present invention includes a crystalline form of anhydrous form 1 of (2S,4S)-4-fluoro-1-[4-fluoro-β-(4-fluorophenyl)-L-phenylalanyl]-2-pyrrolidinecarbonitrile p-toluenesulfonic acid salt characterized by a powder x-ray diffraction pattern comprising at least one of the following peaks:

| Two theta (deg)* | d-spacing (angstroms) |
|---|---|
| 6.1 ± 0.2 | 14.4 ± 0.5 |
| 6.4 ± 0.2 | 13.9 ± 0.5 |

-continued

| Two theta (deg)* | d-spacing (angstroms) |
|---|---|
| 7.7 ± 0.2 | 11.5 ± 0.3 |
| 22.2 ± 0.2 | 4.0 ± 0.1 |
| 24.7 ± 0.2 | 3.6 ± 0.1 |

*Using copper K-alpha 1 radiation.

Preferably, the crystalline form has two or more of the aforementioned peaks. More particularly, the crystalline form has a powder x-ray diffraction pattern that is substantially similar to the pattern in FIG. 1. Notably, in a mixture of the compound of formula I with another phase, not all the peaks listed in Table I may be apparent in the mixture's powder diffraction pattern.

Another aspect of the present invention includes a pharmaceutical composition comprising a compound as described herein. More particularly, the present invention includes pharmaceutical compositions comprising anhydrous form 1 of (2S,4S)-4-fluoro-1-[4-fluoro-β-(4-fluorophenyl)-L-phenylalanyl]-2-pyrrolidinecarbonitrile p-toluenesulfonic acid salt.

Furthermore, the present invention should be interpreted to include pharmaceutical compositions that include one or more hydrated form of (2S,4S)-4-fluoro-1-[4-fluoro-β-(4-fluorophenyl)-L-phenylalanyl]-2-pyrrolidinecarbonitrile p-toluenesulfonic acid salt, one or more solvated form of (2S,4S)-4-fluoro-1-[4-fluoro-β-(4-fluorophenyl)-L-phenylalanyl]-2-pyrrolidinecarbonitrile p-toluenesulfonic acid salt, and/or one or more amorphous form of (2S,4S)-4-fluoro-1-[4-fluoro-β-(4-fluorophenyl)-L-phenylalanyl]-2-pyrrolidinecarbonitrile p-toluenesulfonic acid salt.

Preferably, as used herein pharmaceutical compositions include one or more pharmaceutically acceptable carrier, diluent, or excipient.

Another aspect of the present invention includes a method for the treatment or prophylaxis of metabolic disorders, gastrointestinal disorders, viral disorders, autoimmune disorders, dermatological or mucous membrane disorders, compliment mediated disorders, inflammatory disorders, and psychosomatic, depressive, and neuropsychiatric disorders, including, without limitation, diabetes, obesity, hyperlipidemia, psoriasis, intestinal distress, constipation, encephalomyelitis, glumerulonepritis, lipodystrophy, tissue damage, HIV infection, allergies, inflammation, arthritis, transplant rejection, high blood pressure, congestive heart failure, tumors, and stress-induced abortions that includes the administration of a compound of the present invention, including anhydrates, hydrates, and solvates thereof. As follows, one aspect of the present invention also includes a compound of the present invention for use in therapy.

DETAILED DESCRIPTION OF THE INVENTION

As discussed and illustrated throughout this specification, the present invention includes certain solid state crystalline forms. Several methods for characterizing such forms exist, and the invention should not be limited by the methods chosen or the instrumentation used in characterizing the compounds of the present invention. For example, with regard to x-ray diffraction patterns, the diffraction peak intensities in the experimental patterns can vary, as is known in the art, primarily due to preferred orientation (non-random orientation of the crystals) in the prepared sample. As such, the scope of the present invention must be considered in light of the variability of characterization that is appreciated by those skilled in the art.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the terms "anhydrous" and "anhydrate" are used interchangeably. Likewise the terms "hydrous" and "hydrate" are used interchangeably.

In one embodiment, the compound is the anhydrate form 1 of the compound of formula 1. Typically, the anhydrate form 1 has a water content of about 0.02-2.5% w/w water by coulometric KFT preferably below about 1.0% w/w, more preferably below about 0.5% w/w, more preferably about 0.025% w/w.

Importantly, although the above-referenced water contents are noted, the water content should not be considered as descriptive of any particular pharmaceutical composition or formulation comprising the forms of the present invention. Rather, when in admixture with other pharmaceutically acceptable carriers, diluents, or excipients, the water content may be higher or lower. The water contents given above should be considered as descriptive of the specific forms, themselves.

Figure 1:
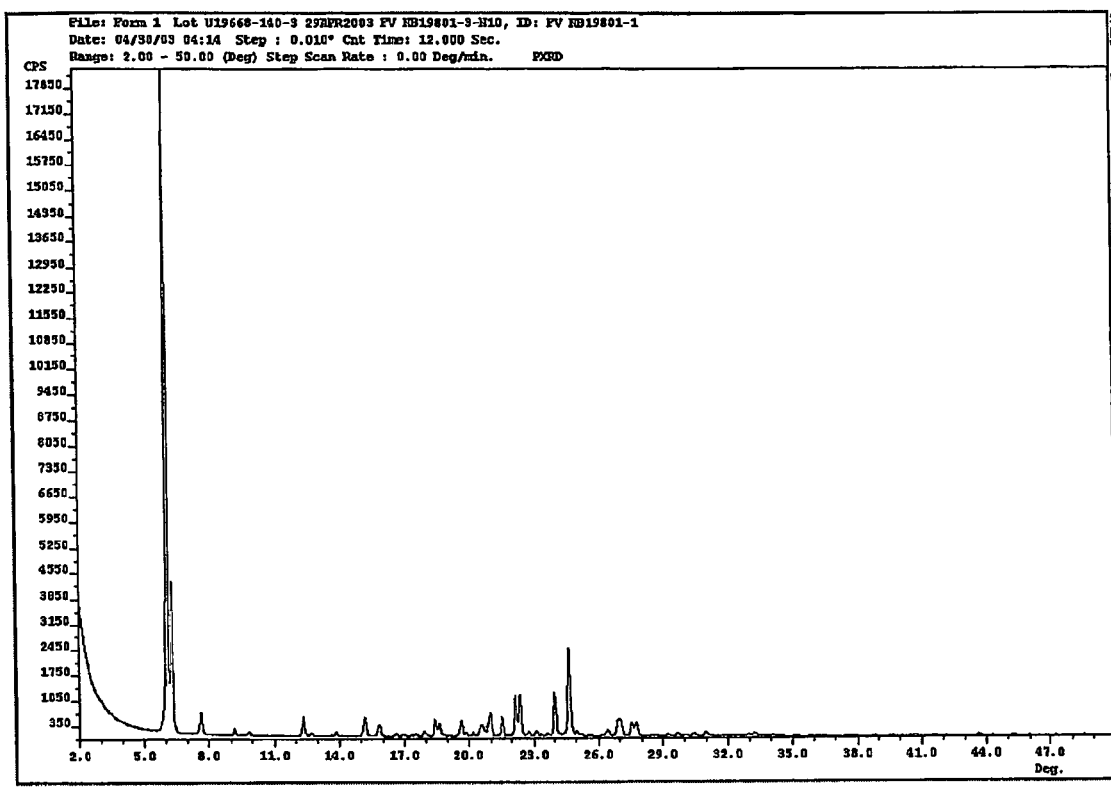
FIG. 1 depicts the powder X-ray diffraction pattern of (2S,4S)-4-fluoro-1-[4-fluoro-β-(4-fluorophenyl)-L-phenylalanyl]-2-pyrrolidinecarbonitrile p-toluenesulfonic acid salt, form 1, using a conventional powder X-ray diffractometer with Bragg-Brentano geometry and copper K alpha radiation.

In one embodiment, the compound is the anhydrate form 1 of the compound of formula I characterized, in part, by a powder x-ray diffraction pattern as shown in FIG. 1. The anhydrate form 1 of the compound of formula I may be characterized by including, but not limited to, the peaks of Table I, below.

TABLE I (Form 1)

| Two theta (deg)* | d-spacing (angstroms) |
|---|---|
| 6.1 ± 0.2 | 14.4 ± 0.5 |
| 6.4 ± 0.2 | 13.9 ± 0.5 |
| 7.7 ± 0.2 | 11.5 ± 0.3 |
| 22.2 ± 0.2 | 4.0 ± 0.1 |
| 24.7 ± 0.2 | 3.6 ± 0.1 |

*Using copper K-alpha 1 radiation.

Notably, in a mixture of the compound of formula I with another phase, not all the peaks listed in Table I may be apparent in the mixture's powder diffraction pattern.

The present invention includes within the scope substantially pure anhydrous, hydrated, or solvate forms, as well as mixtures thereof. The present invention includes within the scope crystalline or amorphous forms and mixtures of crystalline and amorphous forms.

The free base and HCl salt of the compound of Formula I may be prepared according to the procedures of the International Patent Application No. PCT/US02/20471, filed 26 Jun. 2002, and published as WO 03/02531 on 9 Jan. 2003, which application is incorporated herein by reference especially with regard to the experimental procedure therein identified.

As illustrated in Scheme A, the compound of formula 1, namely, (2S,4S)-4-fluoro-1-[4-fluoro-β-(4-fluorophenyl)-L-phenylalanyl]-2-pyrrolidinecarbonitrile p-toluenesulfonic acid salt, has been prepared in one distinct form, an anhydrate designated as Form 1.

Anhydrous Form 1

Form 1 of (2S,4S)-4-fluoro-1-[4-fluoro-β-(4-fluorophenyl)-L-phenylalanyl]-2-pyrrolidinecarbonitrile p-toluenesulfonic acid salt may be prepared by reacting tert-butyl {(1S)-1-[bis(4-fluorophenyl)methyl]-2-[(2S,4S)-2-cyano-4-fluoro-1-pyrrolidinyl]-2-oxoethyl}carbamate in ethanol in the presence of a para-toluenesulfonic acid at elevated temperature, preferably 60° C., followed by cooling and filtration to collect the product.

Alternatively, Form 1 can be isolated when the reaction mixture solvent is acetonitrile, and the reaction is preferably run at 20° C., and the product is isolated by filtration.

Consistent polymorph control of drug substance preparation can be achieved by crystallization from mixtures of water and ethanol.

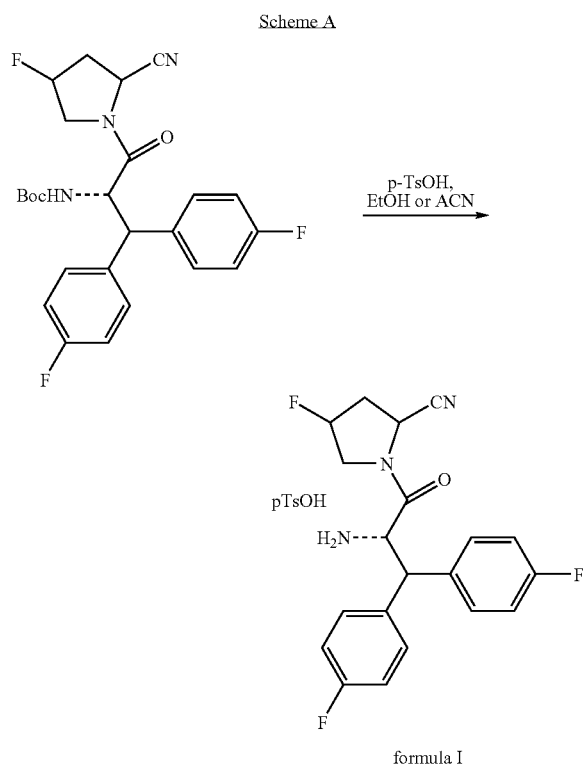

Scheme A

A series of crystallization experiments was performed to investigate whether compound of Formula I can exist in more than one solid-state form or has a propensity to form solvates. This series of experiments employed 47 solvent systems and four crystallization modes (slow evaporation, fast evaporation, cooling, and ripening). These experiments did not indicate the existence of additional non-solvated solid-state forms. There was no evidence of solvated forms from the experiments conducted.

While it is possible that, for use in therapy, therapeutically effective amounts of a compound of the present invention including anhydrate and/or hydrate forms thereof, may be administered as the raw chemical, it is possible to present the active ingredient as a pharmaceutical composition. Accordingly, the invention further provides pharmaceutical compositions which include therapeutically effective amounts of compounds of the present invention including anhydrate and/or hydrate forms thereof, and one or more pharmaceutically acceptable carriers, diluents, or excipients. The compounds of the present invention including anhydrate and/or hydrate forms thereof, are as described above. The carrier(s), diluent(s) or excipient(s) must be acceptable in the sense of being compatible with the other ingredients of the formulation and not deleterious to the recipient thereof. According to another aspect of the invention there is also provided a process for the preparation of a pharmaceutical formulation including admixing a compound of the present invention including anhydrate and/or hydrate forms thereof, with one or more pharmaceutically acceptable carriers, diluents or excipients.

The compound of the present invention including anhydrate and/or hydrate forms thereof may be formulated for administration by any route, and the appropriate route will depend on the disease being treated as well as the subjects to be treated. Suitable pharmaceutical formulations include those for oral, rectal, nasal, topical (including buccal, sublingual, and transdermal), vaginal or parenteral (including intramuscular, sub-cutaneous, intravenous, and directly into the affected tissue) administration or in a form suitable for administration by inhalation or insufflation. The formulations may, where appropriate, be conveniently presented in discrete dosage units and may be prepared by any of the methods well know in the pharmacy art.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compound of the present invention including anhydrate and/or hydrate forms thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compound of the present invention including anhydrate and/or hydrate forms thereof may also be delivered by the use of monoclonal antibodies as individual carriers to which the compound molecules are coupled. The compound may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compound may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference with regard to such delivery systems.

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouthwashes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, Include aqueous or oil solutions of the active ingredient.

Pharmaceutical formulations adapted for administration by inhalation include fine particle dusts or mists, which may be generated by means of various types of metered, dose pressurized aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

In addition to the ingredients particularly mentioned above, the formulations may include other agents conventional in the art having regard to the type of formulation in question, for example those suitable for oral administration may include flavoring agents.

Also provided in the present invention, is a method for inhibiting a post proline/analine cleaving protease, such as a serine protease, such as a dipeptidyl peptidase, such as DPP-IV, which includes administering a therapeutically effective amount of a compound of the present invention including anhydrate and/or hydrate forms thereof, to the mammal. The compounds of the present invention including anhydrate and/or hydrate forms thereof are as herein described.

The determination of a therapeutically effective amount of a compound of the present invention, including anhydrate and/or hydrate forms thereof, will depend on a number of factors. Such factors include, but are not limited to, the age and weight of the mammal, the precise disorder requiring treatment and its severity, the nature of the formulation, and the route of administration. The therapeutically effective amount will ultimately be at the discretion of the attendant physician or veterinarian.

Typically, the compound of the present invention including anhydrate and/or hydrate forms thereof will be given for treatment in the range of 0.1 to 100 mg/kg body weight of recipient (mammal) per day. Acceptable daily dosages, may be from about 0.1 to about 1000 mg/day, and preferably from about 0.5 to about 500 mg/day.

The compound of the present invention including anhydrate and/or hydrate forms thereof, described above, is useful in therapy and in the preparation of medicaments for treating a disorder in a mammal, which is characterized by the need for inhibition of a post proline/analine cleaving protease, such as a serine protease, such as a dipeptidyl peptidase, such as DPP IV. The compound of the present invention including anhydrate and/or hydrate forms thereof is useful for treating or preventing metabolic disorders, gastrointestinal disorders, viral disorders, autoimmune disorders, dermatological or mucous membrane disorders, compliment mediated disorders, inflammatory disorders, and psychosomatic, depressive, and neuropsychiatric disorders, including, without limitation, diabetes, obesity, hyperlipidemia, psoriasis, intestinal distress, constipation, encephalomyelitis, glumerulonephritis, lipodystrophy, tissue damage, HIV infection, allergies, inflammation, arthritis, transplant rejection, high blood pressure, congestive heart failure, tumors, and stress-induced abortions.

The following examples are intended for illustration only and are not intended to limit the scope of the invention in any way.

EXAMPLE 1

Preparation of (2S,4S)-4-fluoro-1-[4-fluoro-β-(4-fluorophenyl)-L-phenylalanyl]-2-pyrrolidinecarbonitrile p-toluenesulfonic acid salt, Form 1 a) Preparation of (4S)-1-(tert-butoxycarbonyl)-4-fluoro-L-prolinamide

A reactor was charged with (4S)-1-(tert-butoxycarbonyl)-4-fluoro-L-proline (130 g, 1 wt, 1 eq.), dichloromethane (520 mL, 4 vol), pyridine (55 mL, 0.4 vol, 1.2 eq), and Boc-anhydride (145 g, 1.1 wt, 1.2 eq.). The reaction solution was stirred at approximately 20° C. for 2 hours. The reactor was charged with ammonium bicarbonate (62 g, 0.5 wt, 1.44 eq), and was stirred at approximately 20° C. overnight. The reaction was filtered over a bed of celite (130 g, 1 wt), and the filter cake was washed with dichloromethane (260 mL, 2 vol). The filtrate was concentrated to a volume of 3 volumes, heptane (520 mL, 4 vol) was added, and again concentrated to a final volume of 3 volumes. Heptane (390 mL, 3 vol) was added, and the reaction was cooled to approx. 5° C. for 30 min.

The solid was collected by filtration, washed with heptane (260 mL, 2 vol), and then dried under vacuum at approximately 50° C. to constant weight. Yield: 88-90%.

b) Preparation of (2S,4S)-4-fluoropyrrolidine-2-carbonitrile para-toluenesulfonic acid The reactor was charged with (4S)-1-(tert-butoxycarbonyl)-4-fluoro-L-prolinamide (116 g, 1 wt, 1 eq.), isopropyl acetate (578 mL, 5 vol), and pyridine (88 mL, 0.8 vol, 2.2 eq). The resulting slurry was stirred at approx. 20° C. Trifluoroacetic anhydride (77 mL, 1.0 wt, 1.1 eq.) was added over at least 30 minutes, maintaining the temperature at approx. 20° C. The reaction solution was stirred an additonal 1 hour at approx. 20° C. Water (578 mL, 5 vol) was added slowly, and the reaction mixture was stirred for 15 minutes. The stirring was stopped, the layers were allowed to separate, and the aqueous (lower) layer was discarded. The organic layer was concentrated under vacuum at a jacket temperature of approximately 50° C. to half volume. The reaction was diluted back up to 5 volumes with isopropyl acetate. The reactor contents were cooled to 20° C., and the reactor was charged with p-toluenesulfonic acid (94 g, 0.8 wt, 1 eq). The reaction was stirred for 2 hours, and GC analysis at this point should show complete consumption of (4S)-1-(tert-butoxycarbonyl)-4-fluoro-L-prolinamide. The reaction was concentrated to 3 volumes under full vacuum at a jacket temperature of approximately 50° C. and 2 volumes of isopropyl alcohol were added. The reaction was concentrated to a final volume of 4 volumes. The reaction was cooled to 0° C. and held for 30 minutes. The solids were collected by filtration, washed with isopropyl alcohol (1 vol), and then dried under vacuum at approx. 50° C. to constant weight. Yield: 68-71%.

c) Preparation of tert-Butyl{(1S)-1-[bis(4-fluorophenyl)methyl]-2-[(2S,4S)-2-cyano-4-fluoro-1-pyrrolidinyl]-2-oxoethyl}carbamate A reactor was charged with N-{[(1,1-dimethylethyl)oxy]carbonyl}-4-fluoro-β-(4-fluorophenyl)-L-phenylalanine (400 g, 1 wt, 1 eq.), (2S,4S)-4-fluoropyrrolidine-2-carbonitrile para-toluenesulfonic acid (307.7 g, 0.77 wt, 1.01 eq.), O-(7-Azabenzotriazol-1-yl)-N,N,N,N-tetramethyluronium hexaflurophosphate [i.e. HATU] (408 g, 1.02 wt, 1.01 equiv.), and DMF (2.8L, 7 vol). The mixture was cooled to approximately 0° C. Hunig's base (376 mL, 0.94 vol, 2.04 equiv.) was added over at least 30 minutes. The mixture was heated to approximately 25° C. and was stirred at this temperature until the reaction was complete (ca. 3 hours). MTBE (2.8L mL, 7 vol) was added, followed by water (2L, 5 vol) over at least 30 minutes to quench the reaction. The aqueous phase was extracted with MTBE (1.2L, 3 vol). The combined organic phases were washed with water (2L, 5 vol). The organic phase was concentrated under vacuum to 3 volumes, and ethanol (1.6L, 4 vol) was added. The reaction was further concentrated under vacuum to 3 volumes, and ethanol (1.6 L, 4 vol) was added. The reaction was further concentrated under vacuum to 3 volumes. Added ethanol (2L, 5 vol). The ethanol solution of tert-Butyl {(1 S)-1-[bis(4-fluorophenyl)methyl]-2-[(2S,4S)-2-cyano-4-fluoro-1-pyrrolidinyl]-2-oxoethyl} carbamatewas used directly in the next step.

d) Preparation of (2S,4S)-4-fluoro-1-[4-fluoro-β-(4-fluorophenyl)-L-phenylalanyl]-2-pyrrolidinecarbonitrile p-toluenesulfonic acid salt. Form 1

A 10L reactor equipped with overhead stirring was charged with a slurry of tert-Butyl {(1S)-1-[bis(4-fluorophenyl)methyl]-2-[(2S,4S)-2-cyano-4-fluoro-1-pyrrolidinyl]-2-oxoethyl}carbamate (500 g, 1 wt, 1 eq) in ethanol (3.5L, 7 vol). To this solution was added para-toluenesulfonic acid (403g, 0.806 wt, 2 eq). This solution was heated to 60° C., and was allowed to stir at this temperature for 12 hours. The reaction mixture was cooled to 5° C. and was stirred at this temperature for 30 minutes. The solids were collected by filtration, washed with ethanol (2×1 L), and dried to constant weight in a 50° C. vacuum oven. Yield: 70-80% over 2 steps.

EXAMPLE 2

Powder X-Ray Diffraction of (2S,4S)-4-fluoro-1-[4-fluoro-β-(4-fluorophenyl)-L-phenylalanyl]-2-pyrrolidinecarbonitrile p-toluenesulfonic acid salt, Form 1

The X-Ray Powder Diffractogram pattern of the anhydrate p-toluenesulfonic acid salt was recorded using the following acquisition conditions: Tube anode: Cu, Generator voltage: 45 kV, Generator current: 40 mA, Start angle: 2.0°2θ, End angle: 50°2θ, Step size: 0.01°2θ, Time per step 12.0 seconds. The X-ray diffraction pattern obtained is shown in FIG. 1 and is included to illustrate but not to limit the present invention.

EXAMPLE 3

Preparation of (2S,4S)-4-fluoro-1-[4-fluoro-β-(4-fluoroohenyl)-L-phenylalanyl]-2-pyrrolidinecarbonitrile hydrochloride

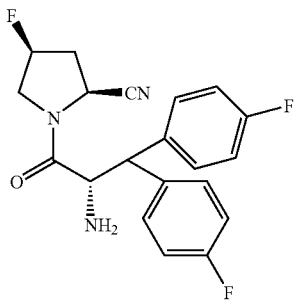

Alternatively, the compound may be named as (2S,4S)-1-[(2S)-2-Amino-3,3-bis(4-fluorophenyl)propanoyl]-4-fluoropyrrolidine-2-carbonitrile hydrochloride.

A. 3,3-Bis(4-fluorophenyl)-3-hydroxypropanoic acid

To an anhydrous THF (80 mL) solution of n-butyl lithium (46 mL of 2.5 M, 115 mmol) at 0° C. was added dropwise diisopropylamine (11.13 g, 115 mmol) and the solution stirred for 10 minutes. Keeping the solution at 0° C., acetic acid (2.64 g, 44 mmol) was added dropwise and the mixture stirred for 10 min and it was then heated 50° C. After 30 min a heavy precipitate had formed and the solution was allowed to cool. A solution of 4,4'-diflurobenzophenone (9.6 g, 0.044 mol) in THF (50 mL, anhydrous) was added at 0° C., and the solution stirred at room temperature overnight. Water (100 mL) and diethyl ether (100 mL) were added and the aqueous layer was separated and acidified with 1 M HCl to pH 3. The organics were extracted with ethyl acetate (3×200 mL) followed by drying over $MgSO_4$. Filtration and removal of the solvent in vacuo yielded a crude white solid that could be washed with cold $CHCl_3$ to remove trace amounts of the benzophenone. The solid was dried under high vacuum yielding 5.63 g (20.2 mmol, 46% yield) of compound A as a white solid.

$^1$H NMR ($d_6$-DMSO) 400 MHz δ 12.4 (s(br), 1H), 7.48-7.39 (m, 4H), 7.19-7.02 (m, 4H), 5.91 (s(br), 1H), 3.25 (s, 2H) ppm.

B. 3,3-Bis(4-fluorophenyl)acrylic acid

To a 20% solution of sulfuric acid in acetic acid (50 mL, V/V) was compound A (5.6 g, 20.2 mmol) and the mixture stirred for 30 minutes at RT. To this solution was added $H_2O$ (500 mL) and the organics were extracted with ethyl acetate (3×150 mL) followed by drying over $MgSO_4$. Filtration and removal of the solvent in vacuo yielded a white solid. The solid was dried under high vacuum yielding 4.97g (19.1 mmol, 95% yield) of compound B as a white solid.

$^1$H NMR ($CDCl_3$) 400 MHz δ 7.27-7.21 (m, 2H), 7.19-7.13 (m, 2H), 7.10-6.95 (m, 4H), 6.26 (s, 1H) ppm.

C. 3,3-Bis(4-fluorophenyl)propanoic acid

To a solution of compound B (2.5 g, 9.61 mmol) in ethyl acetate (250 mL) was added 10% palladium on carbon (50% w/w) and hydrogenated at 1 atmosphere of hydrogen for 12 hours. The heterogeneous solution was filtered through celite and concentrated in vacuo to provide a yellow oil. The oil was dried under high vacuum yielding 2.40 g (9.16 mmol, 95% yield) of compound C as a yellow oil.

$^1$H NMR ($d_6$-DMSO) 400 MHz δ 12.08 (brs, 1H), 7.40-7.30 (m, 4H), 7.15-7.05 (m, 4H), 4.45 (t, 1H, J=8.1 Hz), 3.05(d, 2H, J=8.1 Hz) ppm.

D. (4S,5R)-3-[3,3-Bis(4-fluorophenyl)propanoyl]-4-methyl-5-phenyl-1,3-oxazolidin-2-one To a THF (50 mL, anhydrous) containing compound C (2.0 g, 7.63 mmol) was added N,N-diisopropylethylamine (1.18 g, 9.16 mmol) and then the solution cooled to −78° C. To this solution was added trimethylacetyl chloride (0.97 g, 8.01 mmol) and the solution warmed to 0° C. over 1 hour. The cloudy mixture was filtered and the filtrate added slowly over 10 min to a solution of the lithiated (4S,5R)-(−)-4-methyl-5-phenyl-2-oxazolidinone at −78° C., which was prepared by the dropwise addition of n-butyl lithium (3.0 mL of 2.5 M, 7.63 mmol) to a THF (50 mL) solution of (4S,5R)-(−)-4-methyl-5-phenyl-2-oxazolidinone (1.35 g, 7.63 mmol) at −78° C. which had stirred for 10 min to provide the lithiated (4S,5R)-(−)-4-methyl-5-phenyl-2-oxazolidinone. The yellow mixture was warmed to 0° C. and quenched with $H_2O$ (50 mL) and extracted with diethyl ether (3×250 mL) followed by drying over $MgSO_4$. Filtration and removal of the solvent in vacuo yielded a solid. Flash chromatography (silica gel, 20% ethyl acetate/hexanes) provided compound D. The white solid was dried under high vacuum yielding 2.31 g (5.49 mmol, 72% yield) as a white solid.

$^1$H NMR ($d_6$-DMSO) 400 MHz δ 7.40-7.25 (m, 9H), 7.18-7.02 (m, 4H), 5.76 (d, 1H, J=7.6 Hz), 4.65 (m, 1H), 4.58 (t, 1H, J=7.6 Hz), 3.72 (dd, 1H, J=16.8, 7.0 Hz) 3.57 (dd,1 H, J=16.8, 7.0 Hz), 0.58 (d, 3H, J=6.7 Hz) ppm.

E. (4S,5R)-3-[(2S)-2-Azido-3,3- bis(4-fluorophenyl) propanoyl]-4-methyl-5-[(1E,3Z)-1-methylhexa-1,3, 5-trienyl]-1,3-oxazolidin-2-one To a THF (50 mL, anhydrous) solution containing compound D (2.0 g, 4.75 mmol) at about −78° C. was added dropwise potassium bis(trimethylsilyl)amide (10.0 mL of 0.5 M toluene solution, 4.98 mmol). After stirring for 10 min 2,4,6-triisopropylbenzenesulfonyl azide (trisyl azide) (1.84 g, 5.94 mmol) in THF (10 mL, anhydrous) was added in one portion. After 3 minutes acetic acid was added (1.31 g, 21.8 mmol) at about −78° C. and then the reaction quickly warmed to about 30° C. and stirred for 1 hr at that temperature generating a light yellow solution. To this solution was added $H_2O$ (100 mL) and the organics were extracted with ethyl acetate (500 mL). After washing with sat. $NaHCO_3$ (100 mL) and drying over $MgSO_4$ the solvent was removed in vacuo yielding a yellow oil. Column chromatography (ethyl acetate/hexanes 1:9) provided compound E as a white solid. HPLC showed a single diastereoisomer. The white solid was dried under high vacuum yielding 1.71 g (3.70 mmol, 78% yield) as a white solid.

$^1$H NMR ($CDCl_3$) 400 MHz δ 7.42-7.35 (m, H), 7.25-7.18 (m, H), 7.10-7.06 (m, 2H), 7.05-6.92 (m, 2H), 5.95 (d, 1H, J=10.8 Hz), 5.05 (d, 1H, J=7.1 Hz), 4.60 (d, 1H, J=10.8 Hz), 4.38 (m, 1H), 0.95 (d, 3H, J=6.8 Hz) ppm.

F. (2S)-2-Azido-3,3-bis(4-fluorophenyl)propanoic acid

To a $THF/H_2O$ (4:1, 50 mL) solution of compound E (1.5 g, 3.25 mmol) at 0° C. was added a solution of lithium hydroxide (0.272 g, 6.49 mmol) in hydrogen peroxide (1.50 mL of 30% soln in $H_2O$, 48.75 mmol). The mixture was stirred at 0° C. for 1 hr and then quenched with $Na_2SO_4$ (6.3 g, 50 mL of 1.0 M solution in $H_2O$). The THF was removed in vacuo and the solution acidified to pH 1 with 6.0 M HCl at 0° C. The organics were extracted with ethyl acetate (2×200 mL) followed by drying over $MgSO_4$. Filtration and removal of the solvent in vacuo yielded a clear oil. Column chromatography (EtOAc/hexanes/acetic acid 50:50:1) provided compound F as a white solid. The solid was dried under high vacuum yielding 0.78 g (2.60 mmol, 80% yield) as a white solid.

$^1$H NMR ($CDCl_3$) 400 MHz δ 9.60(s(br), 1H), 7.25-7.10 (m, 4H), 7.10-6.95 (m, 4H), 4.50 (d, 2H, J=8.6 Hz) ppm.

G. (2S)-2-Amino-3,3-bis(4-fluorophenyl)propanoic acid

To an ethyl acetate (250 mL) solution of compound F (1.5 g, 4.95 mmol) was added 10% palladium on carbon (10% w/w) and hydrogenated at 1 atmosphere of hydrogen for 12 hr. The heterogeneous solution was filtered through celite (1 g) and the filtrate concentrated in vacuo to provide a clear oil. The oil was dried under high vacuum yielding 1.30 g (4.70 mmol, 95% yield) of compound G as a white solid.

$^1$H NMR ($d_6$-DMSO) 400 MHz δ 10.2(s(br), 1H), 7.38-7.27(m, 4H), 7.08-6.98 (m, 4H), 4.25 (d, 1H, J=8.3 Hz), 3.95 (d, 1H, J=8.3 Hz) ppm.

H. (2S)-2-[(tert-Butoxycarbonyl)amino]-3,3-bis(4-fluorophenyl)propanoic acid To a $CH_2Cl_2$ (150 mL) solution containing compound G (1.30 g, 4.69 mmol) was added triethylamine (2.37 g, 23.4 mmol) and di-tert-butyl dicarbonate (1.23 g, 5.63 mmol). After stirring for 12 hr $H_2O$ (50 mL) and $CH_2Cl_2$ (300 mL) were added and the solution acidified to pH 3 with 1.0 M HCl. Separation of the ethyl acetate layer followed by drying over $MgSO_4$ and removal of the solvent in vacuo yielded a clear oil. The oil was dried under high vacuum yielding 1.68 g (4.4 mmol, 95% yield) of compound H as a white solid.

$^1$H NMR ($d_6$-DMSO) 400 MHz δ 12.4 (s(br), 1H), 7.35-7.22 (m, 4H), 7.15-6.95 (m, 4H), 4.78 (t,1 H, J=8.9 Hz), 4.25 (d,$_1$ H, J=8.9 Hz), 3.05 (m,1 H), 1.20 (s, 3H), 1.15 (s, 6H) ppm.

I. (2S,4S)-1-[(2S)-2-(tert-Butoxycarbonylpamlno-3, 3-bis(4-fluorophanyl)propanoyl]-4-fluoropyrrolidine-2-carbonitrile To a DMF solution (25 mL, anhydrous) was compound H (1.0 g, 2.65 mmol) and HATU (1.0 g, 2.65 mmol). To this solution was added N,N-diisopropylethylamine (0.462 mL, 2.65 mmol) and after 30 min (2S,4S)-4-fluoro-2-pyrrolidinecarbonitrile 4-methylbenzenesulfonate (0.619 g, 2.12 mmol) and additional N,N-diisopropylethylamine (0.37 mL, 2.12 mmol) were added. This solution was allowed to stir at RT for 12 hr and then saturated sodium bicarbonate (100 mL) was added. The resulting gummy mixture was extracted with ethyl acetate (3×100 mL) and the organics were washed with saturated NaCl (50 mL) followed by drying over $MgSO_4$. Filtration and removal of the solvent in vacuo yielded a clear oil. The oil was chromatographed on silica gel (hexanes/EtOAc 4:1) to provide a white solid. The solid was dried under high vacuum yielding 815 mg (1.72 mmol, 65% yield) of the compound as a white solid.

$^1$H NMR ($CDCl_3$) 400 MHz δ 7.38-7.32 (m, 2H), 7.21-7.15 (m, 2H), 7.12-6.98(m, 4H), 5.15 (d, 1H, J=51 Hz), 5.03 (d, 1H, J=8.9 Hz, 4.89 (d,1 H, J=11.2 Hz), 4.86 (d, 1H, J=8.9 Hz), 4.40 (d, 1H, J=11.2 Hz), 3.83 (ddd, 1H, J=36.8, 12.1, 3.7 Hz), 3.05 (d, 1H, J=12.2 Hz), 2.62 (t, 1H, J=15.3 Hz), 2.25 (m,1 H), 1.38 (s, 9H) ppm.

J. (2S,4S)-1-[(2S)-2-Amino-3,3-bis(4-fluorophenyl) propanoyl]-4-fluoropyrrolidine-2-carbonitrile hydrochloride To compound 1 (0.5 g, 1.05 mmol) was added 4.0 N HCl in 1,4-dioxane (10 mL, 40 mmol) and after 3 hr diethyl ether (100 mL) was added. The resulting precipitate was collected by filtration and after drying under high vacuum 0.41 g (1.0 mmol, 95% yield) of compound A was obtained as a white solid.

$^1$H NMR ($d_6$-DMSO) 400 MHz δ8.42 (s(br), 3H), 7.72-7.66 (m, 2H), 7.38-7.32 (m, 2H), 7.25-7.19 (m, 2H), 7.06-7.0 (m, 2H), 5.38 (d, 1H, J=51 Hz), 4.91 (d, 2H, J=8.8 Hz), 4.82 (d, 1H, J=11.3 Hz), 4.41 (d, 1H, J=11.3 Hz), 3.86 (ddd, 1H, J=39.2, 12.4, 3.1 Hz), 3.45 (q, 1H, J=12.4 Hz), 2.38-2.20 (m, 2H) ppm.

Figure 2A:
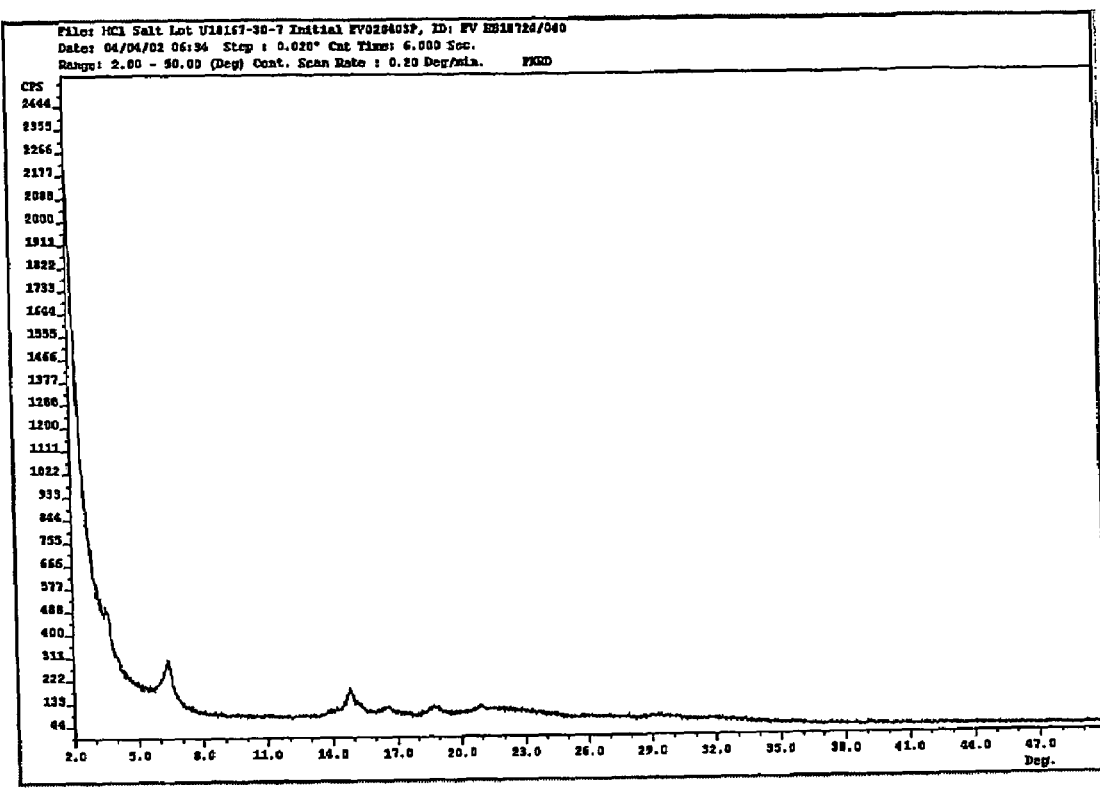
FIG. 2a depicts the powder X-ray diffraction pattern of (2S,4S)-4-fluoro-1-[4-fluoro-β-(4fluorophenyl)-L-phenylalanyl]-2-pyrrolidinecarbonitrile hydrochloride.
Figure 2B:
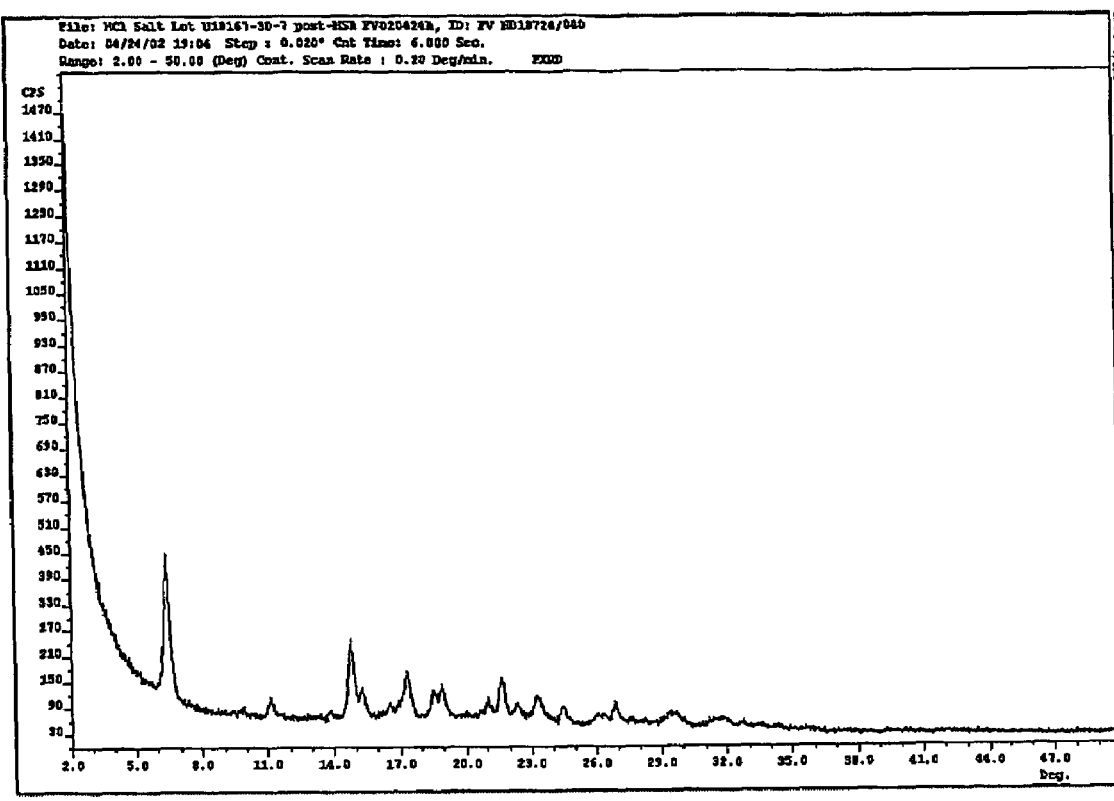
FIG. 2b depicts the powder X-ray diffraction pattern of (2S,4S)-4-fluoro-1-[4-fluoro-β-(4fluorophenyl)-L-phenylalanyl]-2-pyrrolidinecarbonitrile hydrochloride after exposure to 95% relative humidity.

The X-Ray Powder Diffractogram pattern of the anhydrate HCl salt was recorded using the following acquisition conditions: Tube anode: Cu, Generator voltage: 45 kV, Generator current: 40 mA, Start angle: 2.0°2θ, End angle: 50°2θ, Step size: 0.02°2θ, Time per step 6.0 seconds. The X-ray diffraction pattern obtained is shown in FIG. 2a and is included to illustrate but not to limit the present invention.

EXAMPLE 4

Moisture sorption testing of (2S,4S)-4-fluoro-1-[4-fluoro-β-(4-fluorotphenyl)-L-phenylalanyl]-2-pyrrolidinecarbonitrile p-toluenesulfonic acid salt Approximately 35 mg of (2S,4S)-4-fluoro-1-[4-fluoro-β-(4-fluorophenyl)-L-phenylalanyl]-2-pyrrolidinecarbonitrile p-toluenesulfonic acid salt was weighed into a sample pan of a symmetrical integrated gas flow microbalance system (model number SGA-100, manufactured by VTI). The sample was was equilibrated at 25° C. and 30% relative humidity and the relative humidity increased stepwise (adsorption) to 40, 50, 60, 70, 80, 90%—each relative humidity step was held until the sample equilibrated at that condition. Equilibrium was defined as a weight change of less than 0.015% in 5 minutes. The relative humidity was then decreased step wise (desorption) to 90, 80, 70, 60, 50, 40, 30, 20, 10, and 5%—each step held until equilibrium was reached. The equilibrium condition was the same as in the sorption phase. The % w/w increase or decrease in moisture content of the sample is reported for each equilibrated RH condition.

The anhydrate form 1 of the compound of formula I is not hygroscopic; it adsorbs very little water at relative humidity between 5% to 90% at 25° C.

Figure 4:
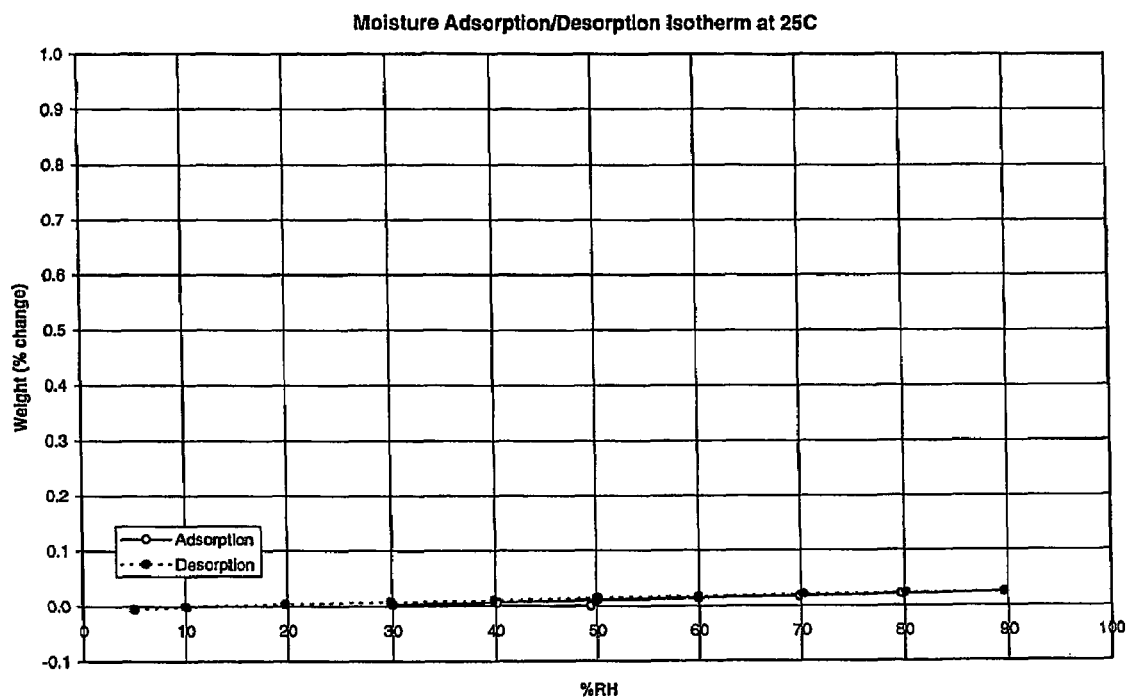
FIG. 4 illustrates the moisture sorption profile of anhydrous form 1

Typically, the anhydrate form 1 adsorbs less than 1% w/w water, preferably less than 0.5% w/w water, more preferably less than 0.2% w/w water at relative humidity between 0% and 95% at 25C. Water adsorbed by anhydrate form 1 readily desorbs when the relative humidity is decreased. See FIG. 4.

EXAMPLE 5

Moisture sorption testing of (2S,4S)-4-fluoro-1-[4-fluoro-β-(4-fluoroohenyl)-L-phenylalanyl]-2-pyrrolidinecarbonitrile HCl salt Approximately 13 mg of (2S,4S)-4-fluoro-1-[4-fluoro-β-(4-fluorophenyl)-L-phenylalanyl]-2-pyrrolidinecarbonitrile HCl salt was weighed into a sample pan of a symmetrical integrated gas flow microbalance system (model number SGA-100, manufactured by VTI). The sample was dried at 60C under a dry nitrogen stream until the rate of weight loss was less than 0.015% in 5 minutes. After drying the sample was equilibrated at 25C and the relative humidity increased stepwise (adsorption) to 5, 20, 45, 75, and 95%—each relative humidity step was held until the sample equilibrated at that condition or a 180 minute time limit was reached. Equilibrium was defined as a weight change of less than 0.015% in 5 minutes. The relative humidity was then decreased step wise (desorption) to 75, 45, and 20%—each step held until equilibrium was reached. The equilibrium condition was the same as in the sorption phase. The % w/w increase or decrease in moisture content of the sample is reported for each equilibrated RH condition.

Figure 5:
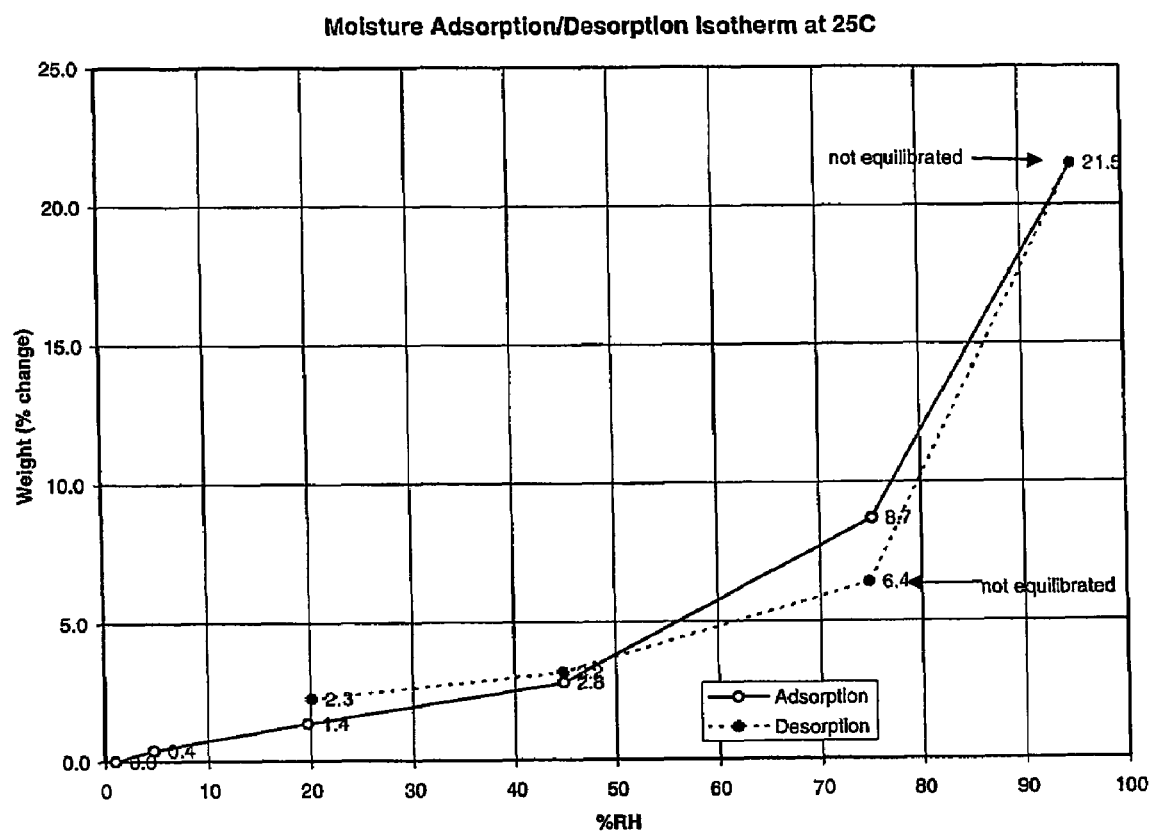
FIG. 5 illustrates the moisture sorption profile of the HCl salt.

The HCl salt of the compound of formula I is hygroscopic, namely it adsorbs about >10% water at 95% relative humidity at 25° C., see FIG. 5.

EXAMPLE 6

Figure 3:
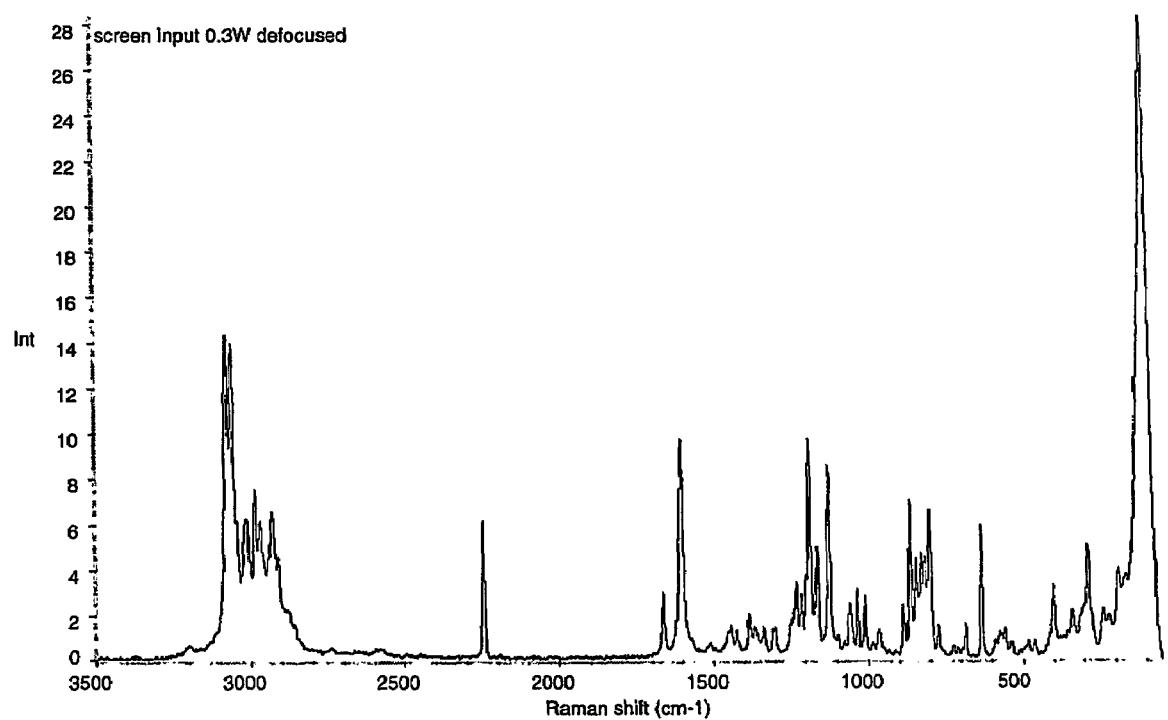
FIG. 3 illustrates FT Raman spectra of form 1.

FT Raman Spectra of (2S,4S)-4-fluoro-1-[4-fluoro-β-(4-fluorophenyl)-L-phenylalanyl]-2-pyrrolidinecarbonitrile p-toluenesulfonic acid salt The FT Raman spectrum of form 1 appears in FIG. 3.

This spectrum of the pure solid was acquired on a Thermo Nicolet 960 FT Raman spectrometer equipped with a Nd:YVO$_4$ laser and View Stage provided by the vendor. The excitation laser is 1064 nm with a laser power of ~300 mW. The spectral resolution was 4 cm$^{-1}$ and 64 scans were averaged to improve the S/N ratio. The peak positions were determined using the "peak find" function provided by the vendor. A number of selected major peaks are listed here: 3078, 3062, 3013, 2987, 2969, 2931, 2246, 1663, 1601, 1187, 1162, 1126, 1034, 1011, 864, 800, 636, 401, 290, 108 cm$^{-1}$. As noted herein, due to the variability appreciated by those skilled in the art, the presence or absence of certain peaks should not necessarily be interpreted too critically in the characterization of a compound within the scope of the present invention.

EXAMPLE 6

Stability Testing

Upon the collection of data regarding the purity of the compounds of the present invention, the compounds of the present invention show beneficial properties with regard to stability, such as after two (2) weeks in an 40 C/75% RH oven. As such, the forms, and in particular anhydrous form 1 of (2S,4S)-4-fluoro-1-[4-fluoro-β-(4-fluorophenyl)-L-phenylalanyl]-2-pyrrolidinecarbonitrile p-toluenesulfonic acid salt, presents a beneficial profile as a commercially viable medicament.

BIOLOGICAL DATA

Materials:

H-Ala-Pro-pNA·HCl was purchased from BACHEM Bioscience Inc. (product no. L-1115). A 500 mM stock solution was prepared with dimethylsulfoxide and stored at −20° C. Gly-Pro-AMC was purchased from Enzyme System Products (product no. AMC-39) and stored at −20° C. as a 10 mM stock solution in dimethylsulfoxide. Test compound was dissolved to 10 mM in dimethylsulfoxide and this was used as a stock solution for DPP-IV titration assay. Athens Research and Technology, Inc prepared the purified human DPP-IV. The material was isolated from human prostasomes using the method of DeMeester et al., J. Immunol. Methods 189, 99-105. (1996), incorporated herein by reference to the extent of describing such method.

DPP-IV Assay:

Two-fold serial dilutions of test compounds in 100% dimethylsulfoxide were performed in 96-well polystyrene flat bottom plates (Costar, #9017). The average enzymatic activity from wells containing dimethylsulfoxide but lacking test compound was used as a control value for calculating percent inhibition. DPP-IV (20 ng/mL) was mixed in microtiter plates with test compound, substrate and assay buffer to yield 100 μM H-Ala-Pro-pNA·HCl in 25 mM Tris, pH 7.5, 10 mM KCl, 140 mM NaCl. The intact peptide contains a p-nitrophenylanilide which, when hydrolyzed by DPP-IV, releases the absorbant p-nitrophenylaniline. The absorbency was monitored in 20 minutes intervals at a wavelength of 387 nm using a Molecular Devices SpectraMax 250 absorbency plate reader. The enzymatic activity was determined by estimating the best linear fit to the data. Values for enzymatic activity were taken directly from the linear fit determined by the software on the plate reader.

Data Analysis: The enzymatic activity was determined by estimating the best linear fit to the data. Data reduction was performed using the Microsoft Excel RoboSage.

Determination of IC$_{50}$ values: The enzymatic activity was plotted against the concentration of test compound, including [I]=0, and the IC$_{50}$ determined from a fit of equation (2) to the data.

$$\text{RATE} = V_{max}/(1+([I]/IC_{50})) \tag{2}$$

$V_{max}$ was the best fit estimate of the maximal enzymatic activity.

Determination of $K_i$ values: $K_i$ values were calculated from $IC_{50}$ values using equation (3) assuming a competitive model.

$$K_i = IC_{50} * \left[1 - \frac{S}{(S + K_m)}\right] \quad (3)$$

The apparent $pK_i$ values for the test compound was >5.0.

All research complied with the principles of laboratory animal care (NIH publication No. 85-23, revised 1985) and GlaxoSmithKline policy on animal use.

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims. Furthermore, when identifying peaks associated with the forms of the present invention, such diffraction patterns should be considered as including such peaks but not limited thereto.

What is claimed is:

1. A crystalline form of anhydrous form 1 of (2S,4S)-4-fluoro-1-[4-fluoro-β-(4-fluorophenyl)-L-phenylalanyl]-2-pyrrolidinecarbonitrile p-toluenesulfonic acid salt characterized by a powder x-ray diffraction pattern comprising at least one of the following peaks:

| Two theta (deg)* | d-spacing (angstroms) |
|---|---|
| 6.1 ± 0.2 | 14.4 ± 0.5 |
| 6.4 ± 0.2 | 13.9 ± 0.5 |
| 7.7 ± 0.2 | 11.5 ± 0.3 |
| 22.2 ± 0.2 | 4.0 ± 0.1 |
| 24.7 ± 0.2 | 3.6 ± 0.1 |

*Using copper K-alpha 1 radiation.

2. The crystalline form of claim 1 comprising two or more of the following peaks:

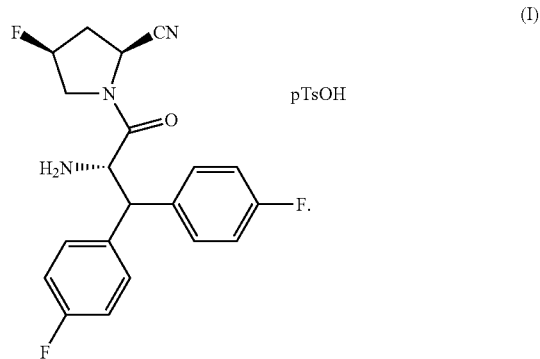

(I)

* * * * *